(12) United States Patent
Mu

(10) Patent No.: US 12,109,057 B2
(45) Date of Patent: Oct. 8, 2024

(54) MEDICAL IMAGING SYSTEMS AND METHODS OF USING THE SAME

(71) Applicant: Argospect Technologies Inc., Foster City, CA (US)

(72) Inventor: Zhiping Mu, Foster City, CA (US)

(73) Assignee: ARGOSPECT TECHNOLOGIES INC., Foster, CA (US)

(*) Notice: Subject to any disclaimer, the term of this patent is extended or adjusted under 35 U.S.C. 154(b) by 215 days.

(21) Appl. No.: 17/856,559

(22) Filed: Jul. 1, 2022

(65) Prior Publication Data
US 2022/0346734 A1    Nov. 3, 2022

Related U.S. Application Data

(62) Division of application No. 16/844,950, filed on Apr. 9, 2020, now Pat. No. 11,375,963.

(60) Provisional application No. 62/832,082, filed on Apr. 10, 2019.

(51) Int. Cl.
| | |
|---|---|
| *A61B 6/06* | (2006.01) |
| *A61B 6/00* | (2006.01) |
| *A61B 6/40* | (2024.01) |
| *A61B 6/42* | (2024.01) |

(52) U.S. Cl.
CPC ............. *A61B 6/4233* (2013.01); *A61B 6/06* (2013.01); *A61B 6/4035* (2013.01); *A61B 6/4447* (2013.01); *A61B 6/5211* (2013.01); *A61B 6/548* (2013.01)

(58) Field of Classification Search
CPC .. A61B 6/42; A61B 1/00; A61B 6/032; A61B 6/02; A61B 6/06; A61B 6/08; A61B 6/4208; A61B 6/4266; A61B 6/425; A61B 6/4275; A61B 6/4283; A61B 6/4429; A61B 6/4291; A61N 5/1045; G21K 1/025;
(Continued)

(56) References Cited

U.S. PATENT DOCUMENTS

| | | |
|---|---|---|
| 7,117,588 B2 | 10/2006 | Vafi et al. |
| 7,989,773 B2 | 8/2011 | Jadrich et al. |
| 9,064,611 B2 | 6/2015 | Freund et al. |

(Continued)

FOREIGN PATENT DOCUMENTS

| | | | |
|---|---|---|---|
| CN | 104854662 B | * 11/2017 | ............. G21K 1/025 |
| CN | 108135554 A | 6/2018 | |

(Continued)

OTHER PUBLICATIONS

International Searching Authority, Notification of Transmittal of the International Search Report and the Written Opinion of the International Searching Authority, or the Declaration, Jul. 9, 2020, International Application No. PCT/US20202/027696, 11 pages, US.

*Primary Examiner* — Don K Wong
(74) *Attorney, Agent, or Firm* — HAYNES AND BOONE, LLP

(57) ABSTRACT

A medical imaging system includes a collimator having a plurality of collimator parts configured to filter radiation emitted from a target object; a detector base; and a detector having a plurality of detector tiles, configured to acquire an image of the target object by detecting radiation that has passed through the plurality of collimator parts, wherein at least one of the plurality of detector tiles is tilted with respect to the detector base.

20 Claims, 11 Drawing Sheets

(58) Field of Classification Search
CPC . G21K 1/04; G21K 1/02; G01T 1/243; G01T 1/244; G01T 1/24
See application file for complete search history.

(56) References Cited

U.S. PATENT DOCUMENTS

| | | |
|---|---|---|
| 9,179,126 B2 | 11/2015 | El-Ghouroury et al. |
| 11,375,963 B2 * | 7/2022 | Mu .................... A61B 6/5211 |
| 2002/0148970 A1 | 10/2002 | Wong |
| 2012/0263276 A1 | 10/2012 | Schubert et al. |
| 2013/0028379 A1 | 1/2013 | Nelson et al. |
| 2013/0259191 A1 | 10/2013 | Koehler et al. |
| 2013/0315376 A1 | 11/2013 | Safai |
| 2014/0284485 A1 | 9/2014 | Nagano et al. |
| 2015/0078525 A1 | 3/2015 | Hofmann |
| 2017/0202528 A1 | 7/2017 | Roessl et al. |

FOREIGN PATENT DOCUMENTS

| | | |
|---|---|---|
| CN | 109211953 A | 1/2019 |
| DE | 10317677 A1 | 11/2004 |

* cited by examiner

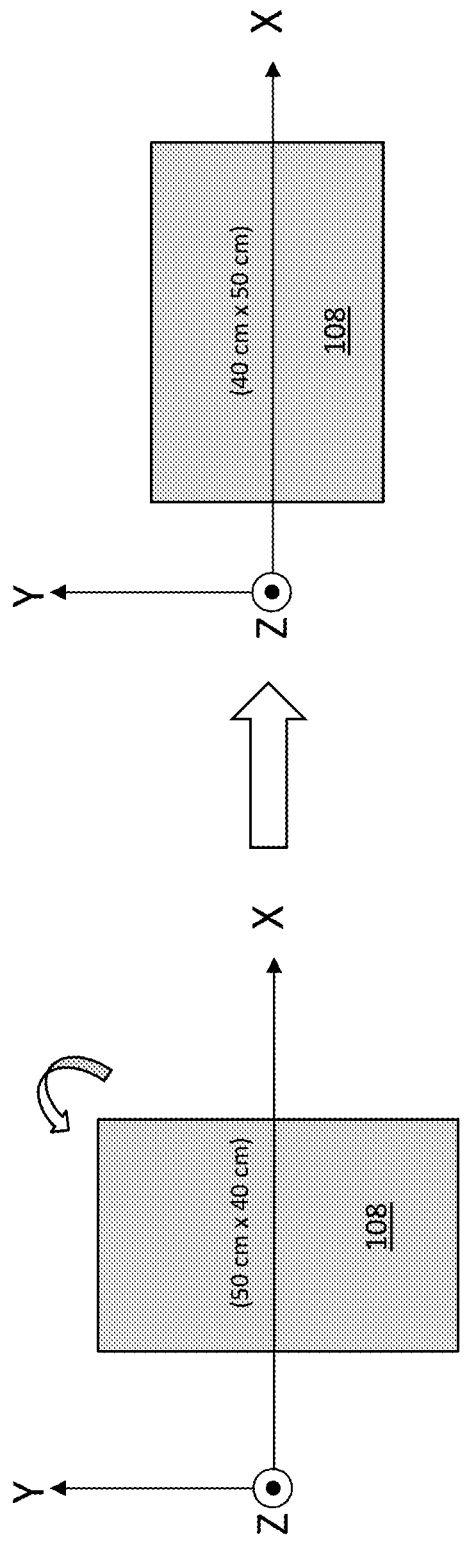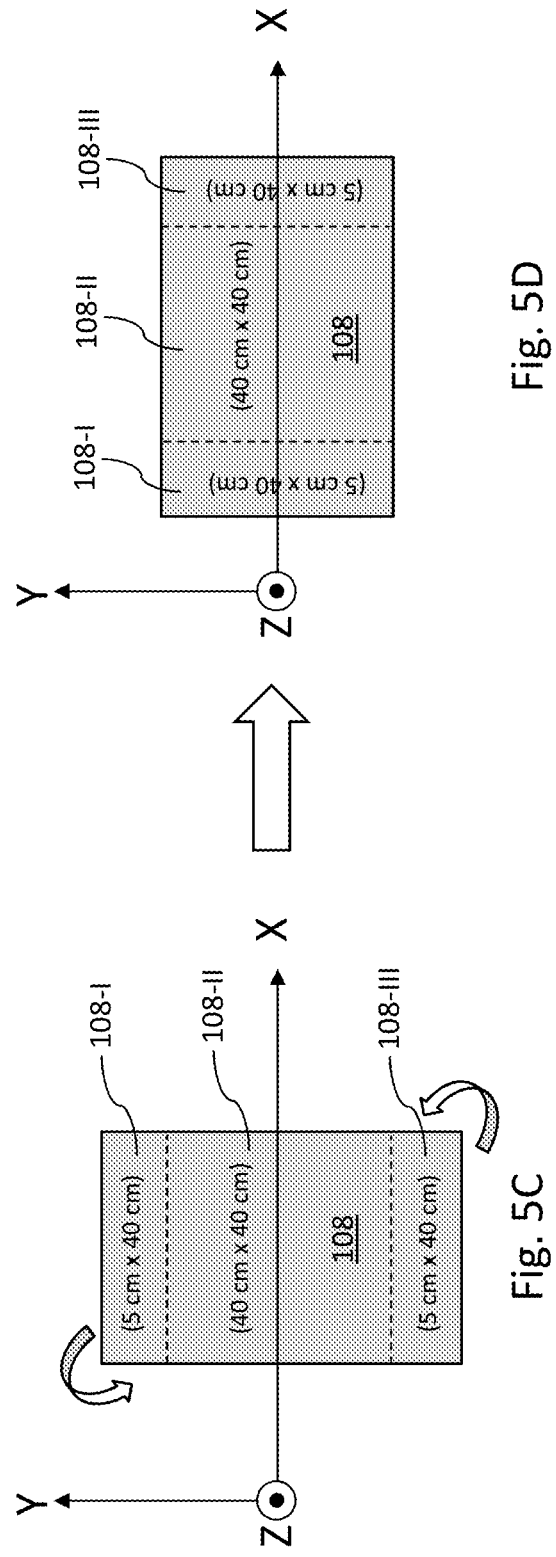

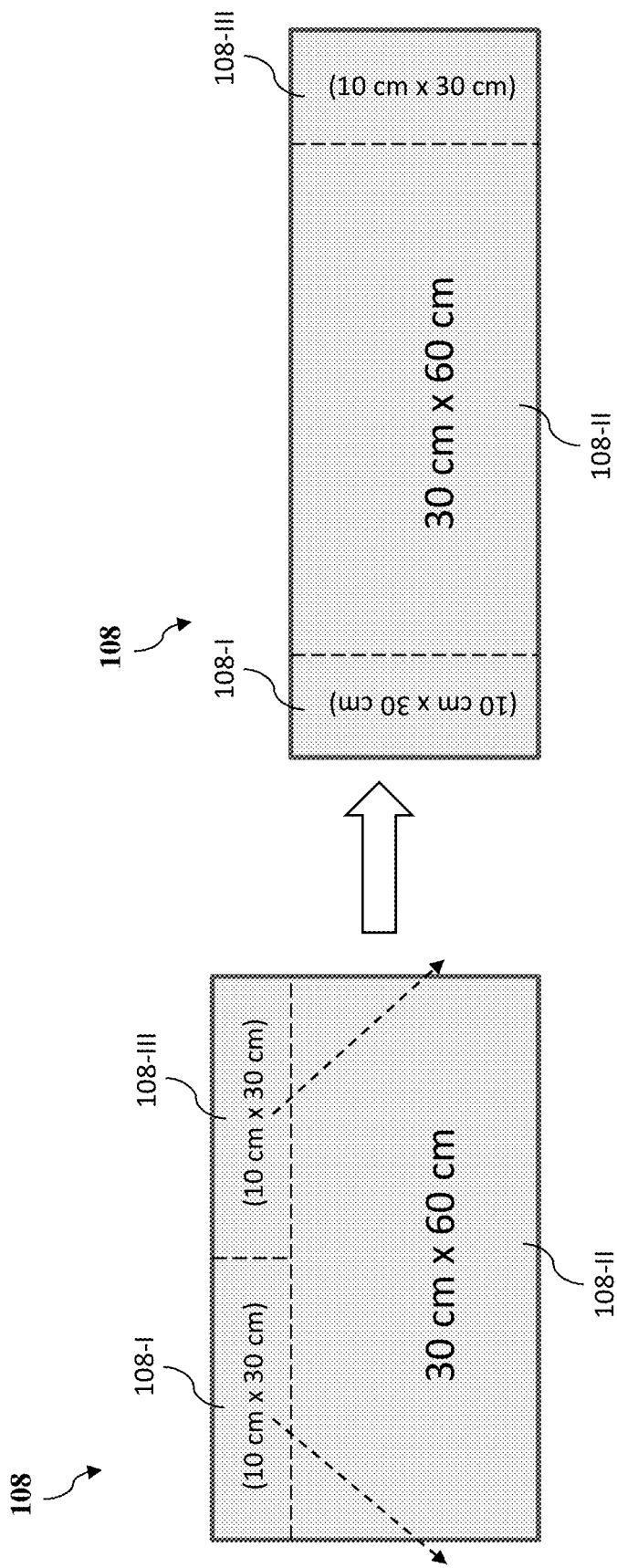

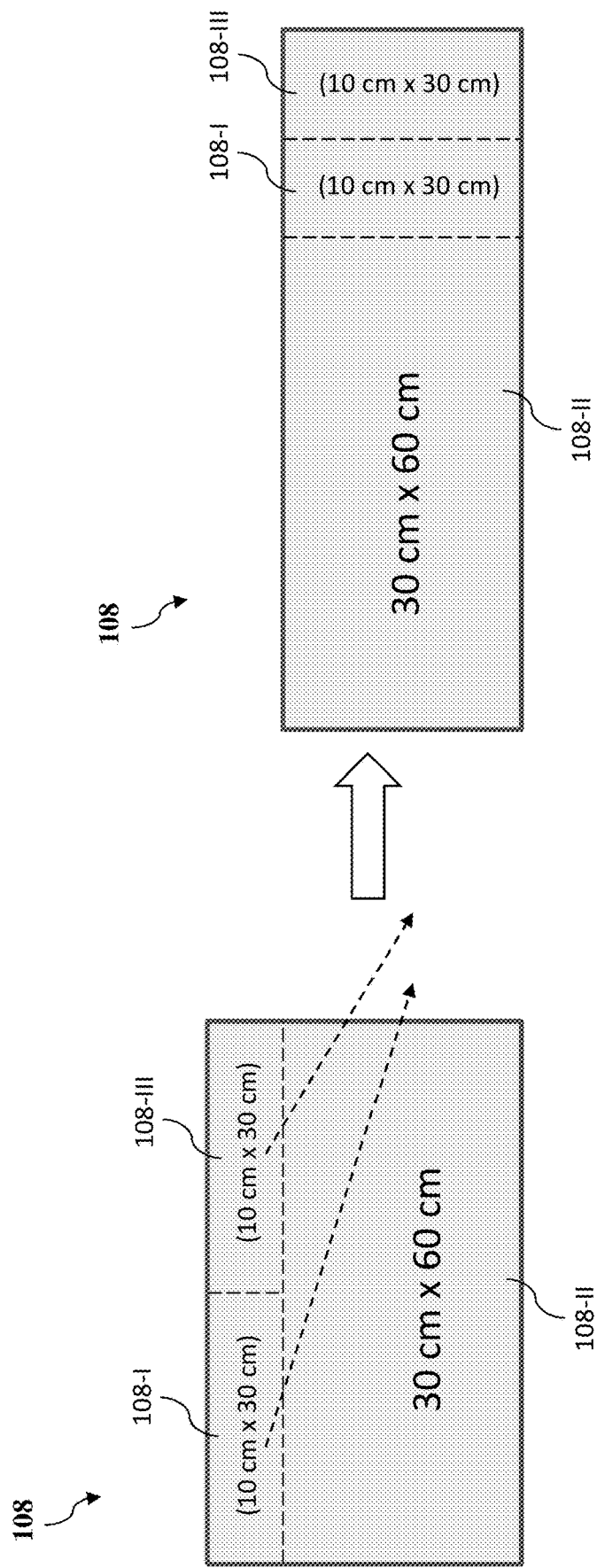

MEDICAL IMAGING SYSTEMS AND METHODS OF USING THE SAME

PRIORITY

This application is a divisional of U.S. patent application Ser. No. 16/844,950 filed on Apr. 9, 2020, which claims priority to U.S. Provisional Application Ser. No. 62/832,082 filed on Apr. 10, 2019, both of which are incorporated herein by reference in their entireties.

BACKGROUND

In medical imaging, such as molecular medical imaging (sometimes known as nuclear medicine imaging), images representing radiopharmaceutical distributions may be generated for medical diagnosis. Prior to imaging, radiopharmaceuticals are injected into an imaging subject such as a patient. The radiopharmaceuticals emit radioactive photons, which can penetrate through the body to be detected by a photon detector. Based on information from the received photons, the photon detector may then determine the distribution of the radiopharmaceuticals inside the patient. Their distribution represents the physiological function of the patient, and therefore images of their distribution provide valuable clinical information for diagnosis of a variety of diseases and conditions such as those in cardiology, oncology, neurology, etc.

To generate images, collimator and detector work in tandem. However, existing collimator and detector designs suffer from various issues. For example, detectors are conventionally organized in planar shapes to acquire data in a two-dimensional (2D) matrix format. Detectors often employ large scintillator crystals coupled with photomultiplier tubes (PMTs) to detect radiations and record their positions. The scintillator-based detector comprises the modules large in size and the position of detected radiation is calculated by comparing the output of neighboring modules. In some examples, the detector employs one piece of scintillator, coupled with multiple PMTs. As a result, a detector is conventionally designed as one piece of a fixed shape and size once deployed (manufactured or installed). The deployment of rigid planar detectors provides a limited degree of spatial resolution and causes inflexibility to the imaging system, limiting system's capability of optimizing for different imaging tasks or subjects. Therefore, improvements on detectors for nuclear medicine imaging systems are desired.

SUMMARY

According to various embodiments, the present disclosure provides a medical imaging system. The medical imaging system includes a collimator configured to filter radiation emitted from a subject; and a detector configured to detect radiation that has passed through the collimator, wherein the detector includes a plurality of detector tiles and at least one detector tile is movable with respect to other detector tiles, wherein top surfaces of the plurality of detector tiles are capable to be configured as being coplanar. In some embodiments, the collimator includes a plurality of collimator parts configured to be piece-wise planar. In some embodiments, each of the plurality of detector tiles is movable. In some embodiments, each of the plurality of detector tile includes a detector base. In some embodiments, the detector base includes a battery pack. In some embodiments, the battery pack is wireless chargeable. In some embodiments, the detector base includes a wireless communication module. In some embodiments, the detector includes a plurality of detector bases, wherein one detector base is shared by at least two detector tiles. In some embodiments, the at least one detector tile is configured to tilt an angle with respect to the other detector tiles. In some embodiments, the at least one detector tile is configured to tilt by an actuator. In some embodiments, the detector is configured to change in shape by moving one or more detector tiles. In some embodiments, the detector is configured to change rotation and keep in shape by moving one or more detector tiles.

According to various embodiments, the present disclosure also provides a medical imaging system. The medical imaging system includes a plurality of collimators configured to filter radiation emitted from a target object; and a detector configured to acquire an image of the target object by detecting the radiation that has passed through the collimator, wherein a portion of the collimators is tilted with respect to a top surface of the detector. In some embodiments, another portion of the collimators is parallel to the top surface of the detector. In some embodiments, the detector includes a plurality of detector tiles, wherein each detector tile is designated with a collimator. In some embodiments, the top surface of the detector is flat. In some embodiments, the portion of the collimators is tilted with an angle larger than 3 degrees with respect to the top surface of the detector. In some embodiments, the medical imaging system further includes a plurality of shields between neighboring collimators.

According to various embodiments, the present disclosure also provides a method for a method of acquiring a medical image. The method includes providing a medical imaging system with a deformable detector, the deformable detector including a plurality of detector tiles; determining a configuration of the deformable detector; moving a portion of the plurality of detector tiles, such that the deformable detector is configured to the determined configuration; and acquiring an image of a targeted subject by the deformable detector. In some embodiments, the method further includes configuring a plurality of collimators associated with the deformable detector.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

FIGS. 5A-5D illustrate embodiment of a detector before and after deformation from a top view according to various aspects of the present disclosure.

FIGS. 6A-6D illustrate alternative embodiments of a detector before and after deformation from a top view according to various aspects of the present disclosure.

DETAILED DESCRIPTION

Figure 1:
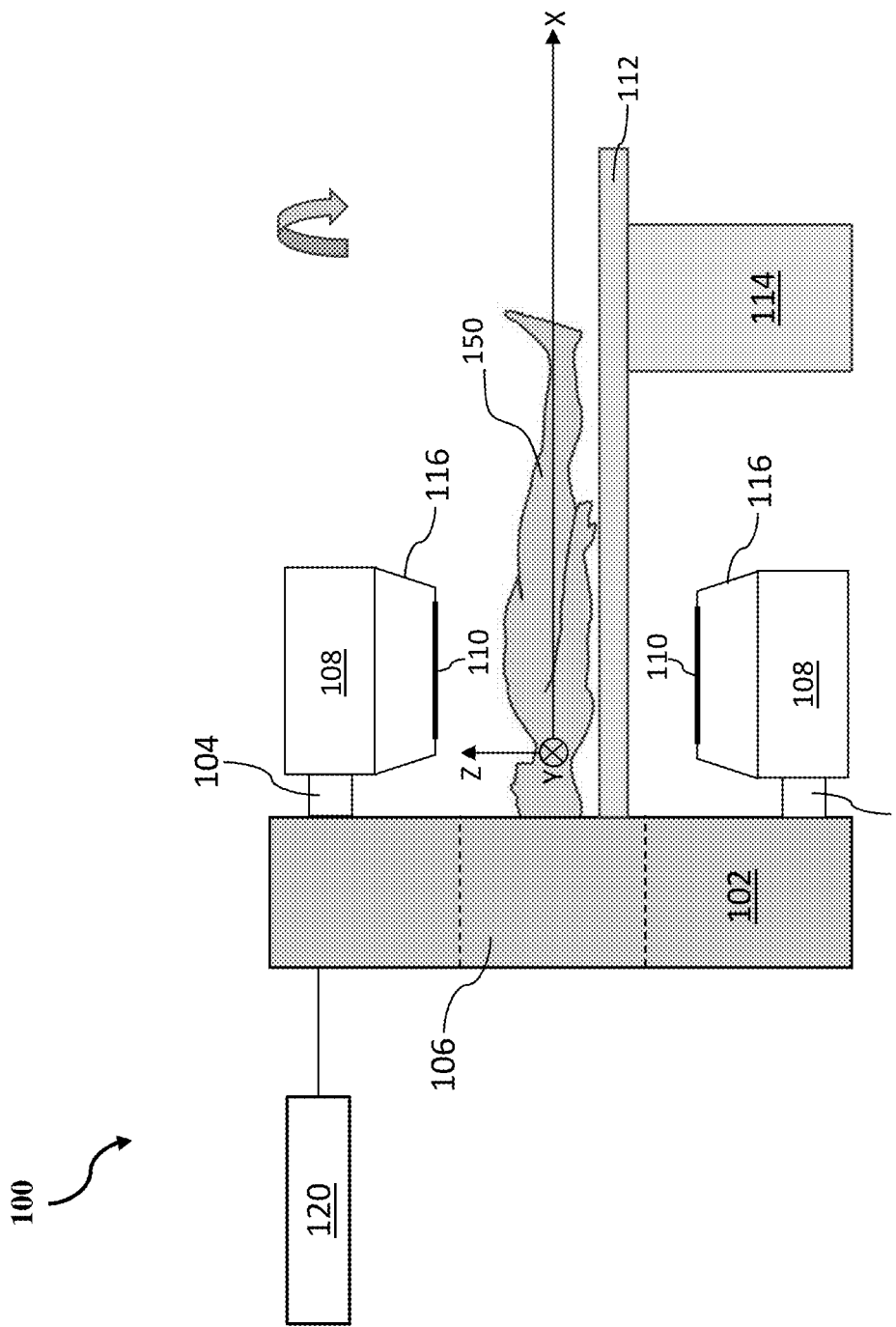
FIG. 1 is a schematic diagram of an exemplary nuclear medicine imaging system according to various aspects of the present disclosure.

The following disclosure provides many different embodiments, or examples, for implementing different features of the disclosure. Specific examples of components and arrangements are described below to simplify the present disclosure. These are, of course, merely examples and are not intended to be limiting. Any alterations and further modifications to the described devices, systems, methods, and any further application of the principles of the present disclosure are fully contemplated as would normally occur to one having ordinary skill in the art to which the disclosure relates. For example, the features, components, and/or steps described with respect to one embodiment may be combined with the features, components, and/or steps described with respect to other embodiments of the present disclosure to form yet another embodiment of a device, system, or method according to the present disclosure even though such a combination is not explicitly shown. In addition, the present disclosure may repeat reference numerals and/or letters in the various examples. This repetition is for simplicity and clarity and does not in itself dictate a relationship between the various embodiments and/or configurations discussed.

Moreover, a feature on, connected to, and/or coupled to another feature in the present disclosure that follows may include embodiments in which the features are in direct contact, and may also include embodiments in which additional features may interpose the features, such that the features may not be in direct contact. In addition, spatially relative terms, for example, "lower," "upper," "horizontal," "vertical," "above," "over," "below," "beneath," "up," "down," "top," "bottom," etc., as well as derivatives thereof (e.g., "horizontally," "downwardly," "upwardly," etc.) are used for ease of the present disclosure of one features relationship to another feature. The spatially relative terms are intended to cover different orientations of the device including the features. Still further, when a number or a range of numbers is described with "about," "approximate," and the like, the term is intended to encompass numbers that are within a reasonable range including the number described, such as within +/−10% of the number described or other values as understood by person skilled in the art. For example, the term "about 5 cm" encompasses the dimension range from 4.5 cm to 5.5 cm.

The present disclosure is generally related to the field of medical imaging, and more particularly to the design of deformable detectors used in nuclear medicine (molecular) imaging systems. The term "deformable" refers to being capable of changing shapes, geometries, areas, alignments and/or orientations.

In nuclear medicine (molecular) imaging systems, collimator and detector work in tandem to generate images that represent radiopharmaceutical distributions within a subject. However, existing collimator and detector designs suffer from various issues. For example, detectors are conventionally organized in planar shapes to acquire planar projections of the object from multiple angles to reconstruct a three-dimensional (3D) image of the object. Conventional detectors employ large scintillator crystals coupled with photomultiplier tubes (PMTs) to detect radiations and record their positions. The scintillator-based detector comprises the modules large in size and the position of detected radiation is calculated by comparing the output of neighboring modules. In some examples, the detector employs a continuous (one piece) scintillator, coupled with multiple PMTs. For example, a type of multi-anode PMT may have a fixed area of 52 cm×52 cm. Therefore, a conventional detector is designed as one module of fixed shape and size once deployed (manufactured or installed). The deployment of rigid planar detectors provides a limited degree of spatial resolution and causes inflexibility to the imaging system.

The present disclosure provides new detector designs where a detector includes multiple detector modules (or detector tiles). Each module further includes multiple cells and each cell acts individually to generate images. The cell is also termed as a pixel. The detector may deform, changing in shapes and/or sizes, by rearranging detector tiles. This deformable detector design provides flexibility to the imaging systems, which helps with optimizing imaging performance for different targets and applications. Therefore, system performance may be improved.

Many medical imaging systems, for example, single photon emission computed tomography (SPECT), computed tomography (CT), and positron emission tomography (PET) imagining systems, use one or more detectors, to acquire imaging data, such as gamma ray or photon imaging data. Prior to acquiring images, a radiopharmaceutical is usually taken orally or injected into the patient. The radiopharmaceutical undergoes nuclear decay, emitting, either directly or indirectly through annihilation, gamma photons at certain rates and with characteristic energies. One or more detector units are placed around the patient or object to record or monitor emissions. In many cases, for convenience of manufacturing and data processing, the detectors are organized in planar shape, therefore acquire data in 2D matrix format, which are often referred to as projections. Based the recorded information including position, energy and counts of such detected events, an image of the radiopharmaceutical distribution can be reconstructed to study the function of certain body parts.

FIG. 1 illustrates an exemplary nuclear medicine imaging system 100, which may be used to medically examine or treat a subject such as a patient. The imaging system 100 includes an integrated gantry 102 that further includes a rotor 104 oriented about a gantry central bore 106. The rotor 104 is configured to support one or more detectors 108 (two detectors 108 in opposing positions are shown). The rotor 104 is further configured to rotate axially about an axial axis (e.g., X-direction as shown). Each detector 108 works in tandem with a collimator 110. The collimator 110 is a device that guides photon path. In molecular imaging, photons may originate from unknown locations inside a subject, unlike in X-ray or CT where photons are emitted from a known source (or sources) position. Without collimators 110, photons from all directions may be recorded by detectors 108, and image reconstruction may become difficult. Therefore, collimators 110 are employed to guide possible photon paths so that images can be reconstructed, similar to the role of lens in a photography camera. The imaging system 100 further includes a patient table 112 coupled to a table support system 114, which may be coupled directly to a floor or may be coupled to the gantry 102 through a base. The patient table 112 is configured to be slidable with respect to the table support system 114, which facilitates ingress and egress of a patient 150 into an examination position that is substantially aligned with the axial axis. A control console 120 provides operation and control of the imaging system 100, such as in any manner known in the art. For example, the control console 120 may be used by an operator or technician to control mechanical movements, such as rotating the rotator 104, moving, rotating, or tilting the detectors 108 and collimators 110, and sliding the patient table 112. The imaging system 100 further includes computer components (not shown), such as data storage units, image processors, image storage units, displays, which are for acquiring data and reconstructing nuclear medicine images. In some embodiments, one or more computer components can be partially or entirely located at a remote location (e.g., on the cloud). In some embodiments, one of more of these components may exist locally or remotely.

In some embodiments, the detector 108 is a semiconductor detector, such as one based on cadmium telluride (CdTe), cadmium zinc telluride (CZT), or high purity germanium (HPGe). In some embodiments, the detector 108 is a scintillator (such as sodium iodide (NaI) or caesium iodide (CsI) based) detector. In some other embodiments, the detector 108 may also be a scintillator coupled with compact photo multiplier tubes (PMTs), silicon photomultiplier tubes (SiPMT), or avalanche photodiodes. One or more radiopharmaceuticals orally taken or injected into patient 150 undergo nuclear decay and may emit, either directly or indirectly through annihilation, radiation (e.g., gamma photons) at certain rates and with characteristic energies. The detector 108 is placed near patient 150 to record or monitor emissions. Based on recorded information such as position, energy, and counts of such detected events, an image of radiopharmaceutical distribution may be reconstructed to study the status or function of certain body parts on patient 150.

The collimator 110 includes one or more openings, such as through holes. Depending on number and geometrical placement of through holes, the collimator 110 may be a single-pinhole, multi-pinhole, coded aperture, or extended coded aperture (also known as spread field imaging, SFI) collimator, or other suitable types of collimator. Depending on profiles of through holes, the collimator 110 may be a parallel-hole, fan-beam, or cone-beam collimator, or other suitable types of collimator. The collimator 110 is placed between detector 108 and an imaging object, such as the patient 150, the openings on the collimators determining the directions and angular span from which radiation can pass through to reach certain position on the detector.

In various embodiments, collimators are essentially perforated plates usually made of heavy metal such as lead and tungsten. In some embodiments, the collimator is made of planar plates, usually placed in parallel to the planar detector surface. The thickness of the plate, depending on the energy of photons it is designed to imaging, is large enough to stop the majority of the radiation so that the photons primarily pass through the small pinholes on the plate. For example, for the commonly used isotope, Technetium-99m (99mTc), emitting gamma rays with energy around 140 keV, a 3 mm thickness is usually enough for a plate made of lead, and about 2 mm for tungsten. The thickness needs to be greater to image higher energy gamma rays. These collimators need to be place at certain distance from the detector to allow photons coming from the design field-of-view (FOV) passing the pinhole(s) to spread across the detector surface. A gap between a collimator and a detector in this scenario is usually greater than 3 cm.

The imaging system 100 may include other necessary parts for an imaging gantry such as connectors that couple parts together (e.g., connecting detector 108 and collimator 110 together), motors that cause parts to move, photon shielding components, a housing component that contains other parts, etc. For example, a coupling and shielding component 116 may connect detector 108 and collimator 110 such that both move (e.g., rotate) together, and prevent radiation (photons) from reaching detector 108 through paths other than collimator 110. In other embodiments, detector 108 and collimator 110 may move individually with respect to each other.

Figure 2:
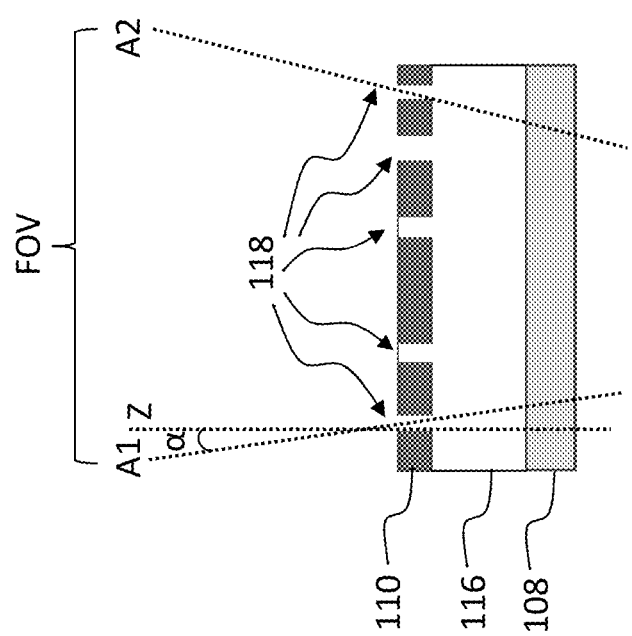
FIG. 2 is a cross-sectional view of part of an imaging system according to various aspects of the present disclosure.

FIG. 2 is a schematic cross-sectional view of a collimator 110 and a detector 108 work in tandem to generate images that represent radiopharmaceutical distributions within a subject. In the illustrated embodiment, a coupling and shielding component 116 connects the collimator 110 and the detector 108. The collimator 110 is positioned between the patient 150 and the detector 108 and configured to filter radiation by blocking certain photons and passing through other photons. Collimator 110 is made of radiation (e.g., photons) absorbing heavy metal(s) or alloy, such as lead and/or tungsten. Collimator 110 has openings 118 built therein to allow some photons to pass through and reach detector 108. It should be understood that radiation or photon blocking or absorption by a collimator does not require blocking of 100% of photons because a small percentage of photons (e.g., 5% or less) may still penetrate through the full thickness of the radiation absorbing material. The number of escaping photons may decrease exponentially with the thickness of a collimator. In other words, blocking (or other similar terms) means that substantially all of the photons (e.g., 95% or more, or 99% or more) are absorbed by the radiation absorbing material.

Openings 118—which may also be called through holes, tunnels, apertures, or pass-through features—may have any suitable shape, size, number, and/or distribution within their respective collimators. In some embodiments, openings 118 may include parallel holes, fan beams, cone beams, slit-slat, pinholes, multi-pinholes, coded aperture, any other suitably shaped openings, or combinations thereof. In some embodiments, collimator 118 is placed close (e.g., 2 cm or less) to patient 150. Thus, collimator 108 may use parallel holes or fan-beams (converging or diverging) since such features do not need significant separation from patient 150. In some embodiments, openings 118 may be slanted, converging, or diverging and may form fan beams or cone beams, etc. In an example, openings 118 include a plurality of pinholes, where the number of pinholes may be greater than 11, greater than 23, or greater than 59, or greater than 83. Openings 118 may form a coded aperture pattern, for example, an MURA (modified uniformly redundant array) of sizes 5, 7, 11, and 13 comprise 12, 24, 60, and 84 holes, respectively. A higher number of pinholes helps improve imaging sensitivity. Further, openings 118 may be single pinhole, multi-pinhole, multiple pinhole modules (including spread field imaging (SFI) or coded aperture).

Still referring to FIG. 2, a photon may hit a top surface of collimator 110 with an acceptable incident angle (denoted by symbol $\alpha$ in FIG. 2 as an angle between line A1 and the vertical direction Z where line A1 is the travel direction of the photon and direction Z is the normal of the top surface of collimator 110). If the incident angle is greater than a predetermined threshold value, the photon would be absorbed by collimator 110 (note there are occasions where the photon cuts through a portion of collimator 110 adjacent the opening (e.g., a thin area on the sidewall of the opening)). Therefore, the acceptable incident angle α represents the range of possible incident angles for photons to pass through an opening 118 without cutting through a portion of collimator 110.

In some embodiments, this threshold value ranges from 0° to about 2° or from 0° to about 10°. In an example, a LEHR (low energy high resolution) collimator has an opening diameter of about 1.11 mm and a length of about 24.04 mm, with an acceptable incident angle range of 0° to about 2.64°. In another example, a GAP (general all purpose) collimator has an opening diameter of about 1.40 mm and a length of about 25.4 mm, with an acceptable incident angle range of 0° to about 3.15°). In yet another example, a LEHS (low energy high sensitivity) collimator has an opening diameter of about 2.54 mm, a length of about 24.04 mm, with an acceptable incident angle range of 0° to about 6.03°. The acceptable incident angle for collimator 110 is often less than 10°. Photons that can pass through collimator 110 is considered within a field-of-view (FOV) of collimator 110 (denoted in FIG. 2 as a space within lines A1 and A2).

In various embodiments of the present disclosure, the detector 108 are formed by multiple detector modules, which is also referred to as detector tiles or pixelated detectors. For example, the detector 108 may include twenty detector tiles arranged to form a rectangular array of five rows of four detector tiles. Each detector tile individually functions as a mini detector to capture or record emissions. At least one detector tile or each detector tile is movable with respect to other detector tiles, which reconfigures the detector 108 to form different shapes and/or sizes.

Figure 3:
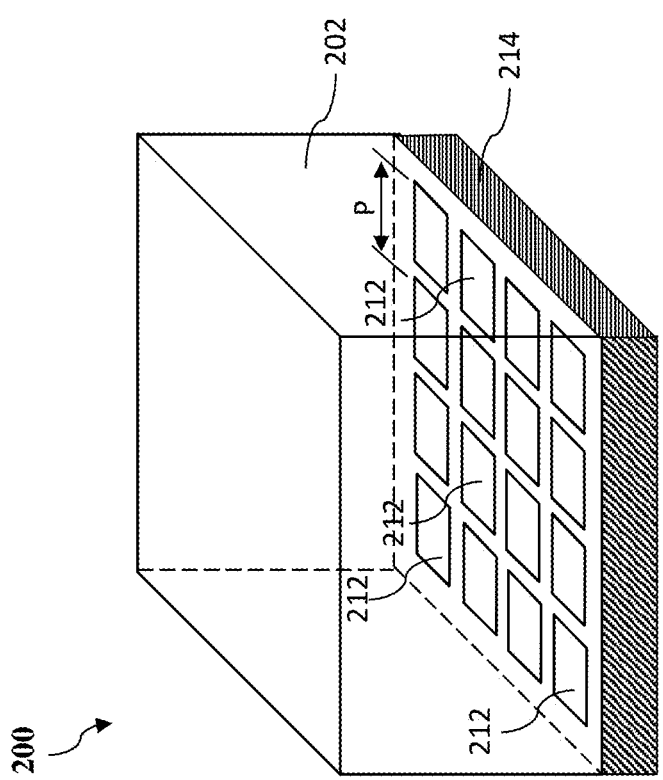
FIG. 3 is a perspective view of an exemplary detector tile according to various aspects of the present disclosure.

FIG. 3 illustrates an exemplary detector tile 200. The detector tile 200 may be formed of any semiconductor material as known in the art, for example, cadmium zinc telluride (CdZnTe), often referred to as CZT, gallium arsenide (GaAs) and silicon multiplier (SiPM), among others. Specifically, the detector tile 200 include a crystal 202 formed from the semiconductor material and mounted on a detector base 214. The bottom surface of the crystal 202 includes an array of pixels 212, such as a rectangular array, a square array, or other suitable arrays. The pixels 212 may be of substantially the same size and also may be rectangular or square in shape. The size of the pixels 212 may range from about 1×1 mm² to about 4×4 mm² in various embodiments. The pixel pitch P of the array may range from less than 1 mm to about 6 mm in various embodiments. Further, in the same array, different pixels 212 may have different sizes or geometries. For example, a portion of the pixels 212 in the center of the array may be larger than the peripheral ones, or vice versa. Also, the number of pixels 212 may be greater or smaller than 16 (4×4) as shown in FIG. 3, for example, 256 (16×16) pixels 212 may be provided. It also should be noted that the thickness of the crystal 202 may vary between several millimeters to several centimeters. The size of the detector tile 200 may range from about 4 cm×4 cm to about 10 cm×10 cm in various embodiments, such as 5 cm×5 cm. And the shape of detector tile does not have to be square, and can be rectangle, hexagon, etc. In a specific example, a CZT or silicon multiplier (SiPM) based detector tile 200 is fabricated in a size of 4 cm×4 cm, further consisting of an array of 16×16 pixels of a unit pixel size of 2.5 mm×2.5 mm. In operation, each pixel 212 records or monitors individually the amount of emission arrived and generates signals (e.g., voltage or current) in association with the amount of emission. In some embodiments, the detector base 214 includes appropriate electronic circuits (e.g., ASICs) to collect and process the signals from the pixels 212.

The detector base 214 may include wired connection units, for example, bus lines (not shown) to transmit singles from the ASICs to the control module 120 (FIG. 1). Alternatively, the detector base 214 may include wireless connection units using technologies such as WiFi and/or Bluetooth, to avoid additional wiring that may cause complication during detector deformation. Furthermore, the detector base 214 may include one or more battery packs to further reduce wiring. The battery packs can be charged during system downtime. The detector base 214 may also include wireless charging units that allow the battery packs to be charged wirelessly. In one example, the detector tile 200 totally eliminates wire connections, relying on wireless data transmission and wireless charging for respective functions. As will be discussed below, multiple detector tiles 200 will jointly form a deformable detector with at least one or each detector tile 200 movable with respect to others. Each of the detector tiles may carry their own battery packs. Alternatively, the battery packs can be mounted to some of the detector tiles that is movable, while the other detector tiles that are fixed can have wire connections to supply power instead of battery packs.

Figure 4:
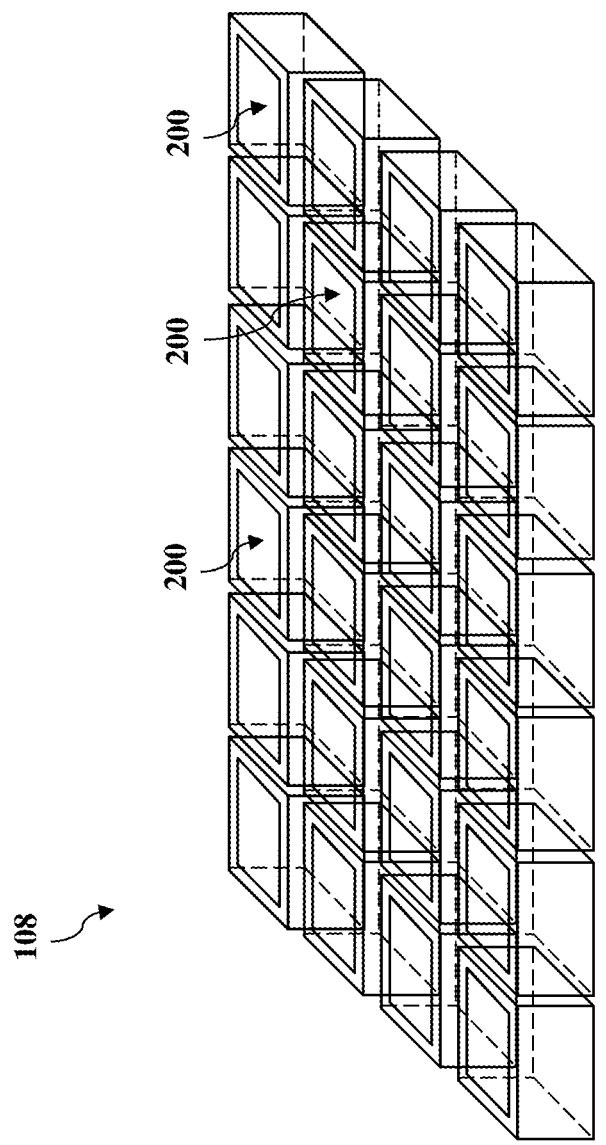
FIG. 4 is a perspective view of an exemplary deformable detector according to various aspects of the present disclosure.

FIG. 4 illustrates a detector 108 that includes a plurality, for example, 24 detector tiles 200 arranged to form a rectangular array of four rows of six detector tiles. It should be noted that the detector 108 may have larger or smaller arrays of detector tiles 200 than as illustrated. Adjacent detector tiles 200 may leave a gap smaller than a predetermined width, such as smaller than a width of a single detector tile 200. The gap may be as small as possible, for example, as physically achievable. In a specific example, the gap is about 5% to about 20% of a single detector tile 200's width. In another example, the gap is less than one pixel pitch P (FIG. 3) or one detector resolution of a detector tile 200, but larger than zero. Alternatively, adjacent detector tiles 200 may be in physical contact (abut) with each other.

Among the detector tiles 200, at least one detector tile 200 may be mounted on a track (e.g., slides or rails). The track is configured to allow that detector tile 200 to move with respect to other detector tiles, thereby changing a contoured geometry of the detector 108. The imaging system may employ robotic arms, with fingers attached to the movable detector tiles 200. Alternatively, each detector tile 200 may be individually movable along the tracks with respect to each other. In some embodiments, the detector 108 may include at least three individually movable groups, such as three, four, five, or six movable detector tiles. In furtherance of some embodiments, detector tiles 200 come with different sizes and/or geometries. For example, one detector tile may be larger than another, or one detector tile has a square shape while another has a rectangular shape. Further, multiple detector tiles 200 may form a group that moves as one unit. Inside the group, locations of the detector tiles 200 are fixed. In furtherance, detector tiles 200 assigned to the same group may share a single battery pack, instead of for each detector tile to carry its own battery pack. And instead of transforming freely, the detector 108 may transform into a few shapes that are predetermined for certain imaging tasks. Thus, a detector 108 may be divided in to a plurality of movable groups with different sizes and/or geometries. In some embodiments, the detector 108 may include at least three individually movable groups, such as three, four, five, or six movable detector tiles. Each individually movable group may include one or more detector tiles 200 with positions relatively fixed inside the group. In furtherance of some embodiments, the smallest movable group consists of only one detector tile 200. In the illustrated embodiment, the top surfaces of all the detector tiles (individually movable or inside a movable group) in a detector 108 are capable to be configured as being coplanar, and in that form the detector tiles are operating as one unity, and image acquired by the detector tiles is stored or represented as one entity such as in the form of one array or one matrix.

FIGS. 5A-5D are top views of the detector 108 in the imaging system 100 in FIG. 1. FIGS. 5A-5D illustrate two embodiments of rotating a rectangular detector without changing its shape or aspect ratio (length/width). FIGS. 5A and 5B illustrate mechanically rotating the detector 108 as a whole. The X-direction marks the axial axis that the patient 150 from head-to-toe lies along. Besides the rotor 104, which provides the rotation of the detector 108 around the axial axis, the imaging system 100 may further has a rotating mechanism mounted on the rotor 104, which allows the detector 108 to rotate around the normal direction of its own. For example, for a detector of size 40 cm×50 cm, the short side (40 cm) is usually aligned with the axial axis in a top view in conventional orientation so that the long side (50 cm) provides maximal coverage in lateral direction (Y-direction) because conventional SPECT systems equipped with a parallel hole collimator provides a FOV of 50 cm diameter. In FIG. 2B, the detector 108 rotates 90 degrees in the X-Y plane around its center, such that the long side is aligned with the axial direction instead, to provide different FOV along axial axis and in cross-sectional plane. In this orientation, the system provides more coverage along the axial direction. One benefit of such orientation is that whole body image may be acquired in smaller number of bed position.

As a comparison, FIGS. 5C and 5D illustrate an example of a deformable detector 108. The deformable detector 108 of size 40 cm×50 cm includes three detector tiles 108-I, 108-II, and 108-III (alternatively, each of 108-I/II/III may include multiple grouped smaller detector tiles). The detector tiles 108-I and 108-III each has a dimension of 5 cm×40 cm, and the detector tile 108-II has a dimension of 40 cm×40 cm. The center detector tile 108-II is fixed, while the other two smaller detector tiles 108-I and 108-II are movable with respect to the center detector tile 108-II. In the illustrated embodiment, the detector tile 108-I slides (e.g., being pushed by a robotic arm) counterclockwise from the top of the center detector tile 108-II to its left side. Similarly, the detector tile 108-II slides counterclockwise from the bottom of the center detector tile 108-II to its right side. The reassembled detector 108 keeps the same shape and size of 40 cm×50 cm but changes its alignment equivalently as after a 90 degrees rotation in the X-Y plane, similar to its counterpart shown in FIG. 5B.

FIGS. 6A and 6B illustrate another example in which a detector 108 may deform into a different shape, with a different aspect ratio. The illustrated example demonstrates a way to transform a detector of size 40 cm×60 cm to 30 cm×80 cm. The detector 108 includes three detector tiles 108-I, 108-II, and 108-III (alternatively, each of 108-I/II/III may include multiple grouped smaller detector tiles). The detector tiles 108-I and 108-III each has a dimension of 10 cm×30 cm, and the detector tile 108-II has a dimension of 30 cm×60 cm. The center detector tile 108-II is fixed, while the other two smaller detector tiles 108-I and 108-III are movable with respect to the center detector tile 108-II. During transformation, the moving paths and directions of detector tiles 108-I and 108-III are denoted with doted arrows. The long edge (30 cm) of the movable detector tile 108-I or 108-III aligns with the short edge (30 cm) of the detector tile 108-II after the transformation. The reassembled detector 108 keeps the same detector area of 2400 $cm^2$, but with an elongated shape and a different aspect ratio (from 60/40 to 80/30).

Different ways of transformation exist. For example, as shown in FIGS. 6C and 6D, detector tile 108-I and 108-III can be rotated and attached to the same side of the detector to achieve the same transformation. During transformation, the moving paths and directions of detector tiles 108-I and 108-III are denoted with doted arrows. Under the similar principle as disclosed herein, depending on sizes of detector tiles or grouped detector tiles, the detector 108 may deform into various other shapes and aspect ratios. For example, a 40 cm×60 cm detector may deform into a 30 cm×80 cm detector as shown in FIGS. 6B and 6C, or a 50 cm×48 cm or a 25 cm×96 cm detector. And this kind of deformation can be easily implemented with detector tiles.

Figure 7:
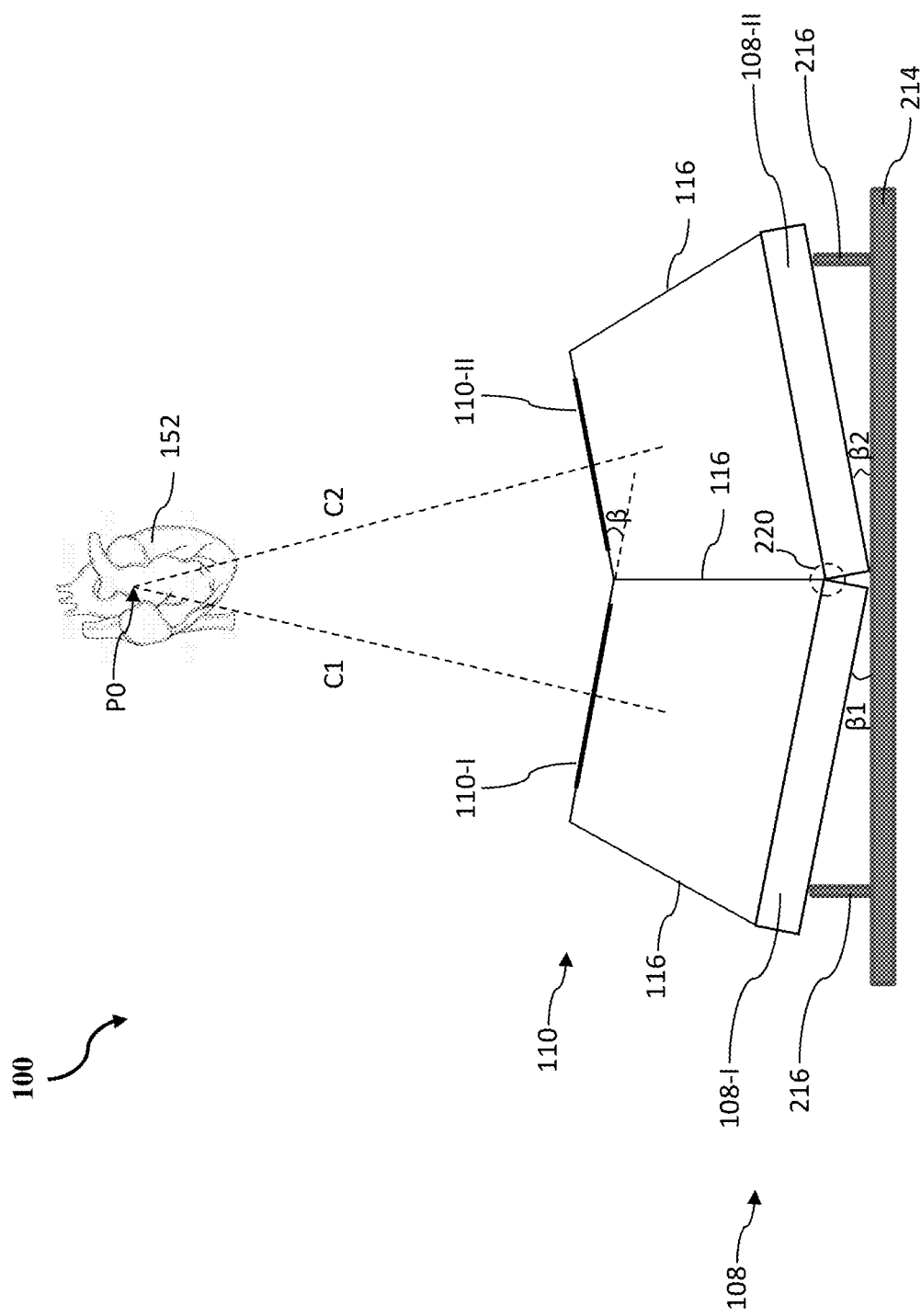
FIG. 7 is a cross-sectional view of an imaging system with bendable detector titles according to various aspects of the present disclosure.

In the illustrated embodiments above, the detector tiles are configured to keep coplanar such that the surface of the detector 108 remains flat. Meanwhile, the detector tiles (or groups of detector tiles) may also be configured to form angles, such as by tilting. FIG. 7 illustrates a cross-sectional view of the imaging system 100 with deformable detector 108 in yet another embodiment. In previous embodiments, before and after the transformation, top surfaces of the detector tiles of the detector 108 are kept coplanar. Besides transforming the detector 108 planarly, the detector tiles may also be tilted by an angle, such as angles β1 and β2 for detector tiles 108-I and 108-II, respectively. In some applications such as imaging a heart 152, the object of imaging is relatively small compared with the detector size. Imaging heart is an important clinical application of SPECT, accounting for about 60% of SPECT scans in the US. In this application, the detector may be bent by being partitioned into several tilted detector tiles. A human heart is usually 12 cm long and 10 cm wide, which is much smaller than the conventional detector size of about 40 cm×50 cm. Because the size of a heart is much smaller than the detector, collimators 110-I and 110-II may be designed in two parts which form a small angle β such as 6 degrees, 8 degrees, 10 degrees, or 12 degrees, to acquire projections at two slightly different angles. In some embodiments, the maximum angle β is limited to be less than about 40 degrees or about 60 degrees. The collimators 110-I and 110-II in such placement is termed angularly placed collimators. The FOV of such angularly placed collimators are overlapping. In some embodiments, the normal lines of these collimator (lines perpendicularly passing through the center of the collimators, denoted as dotted lines C1 and C2 in FIG. 7) intersect at one common point $P_0$ (or a relatively small volume in space where the organ located), which defines the center of FOV of the system in such configuration.

The images of the heart 152 may be projected through the two collimators 110-I and 110-II onto two separate tiles of the detector 108. There is a shielding plate 116 between the two tiles of the detector 108, preventing cross-talk between the two parts, i.e., radiation passing through one collimator and hitting the other tile of the detector. To better receive signals, the detector may be split into two detector tiles which bend slightly so that each tile is parallel to the collimator surface.

Actuators 216 may be used to elevate (tilt) one edge of the detector tile 108-I or 108-II, or both. In some embodiments, actuators 216 extends from the detector base 214. In the illustrated embodiment, the tilted detector tiles 108-I and 108-II form small angles β1 and β2 with respect to the top surface of the detector base 214. Angles β1 and β2 may be the same or different, with the relationship of β1+β2=β. In a specific example, β is 6 degrees, β1 is 2 degrees, and β2 is 4 degrees. By titling detector tiles 108-I and 108-II in different angles, the precise position of the common point $P_O$ can be finely tweaked. The other edges of the detector tiles 108-I and 108-II may stay abut, or have a small gap (e.g., a gap width smaller than a width of the detector tile, or less than 10 cm) in between. In the illustrated embodiment, the two edges may be linked by a hinge 220 and considered as still in physical contact. If the two edges stay in physical contact, the two detector tiles 108-I and 108-II may share one common detector base 214, instead of two separate detector bases, as shown in FIG. 7. In furtherance of the embodiment, if the detector 108 includes three or more tilted detector tiles, the tilted detector tiles may still share one common detector base 214.

The collimators 110-I and 110-II in this case may be pinhole, multi-pinhole, coded aperture, or other suitable forms. One benefit of this design is that multiple projections of the object can be acquired at one detector position. If original imaging requires 60 projections by rotating detector to 60 positions, now it can be done with 30 detector positions. On a dual opposing detectors system which is common for clinical systems (e.g., imaging system 100 in FIG. 1), 60 projections require rotating the two opposing detectors to 30 positions each, now it can be done with only 15 detector positions of the two opposing detectors, reducing imaging time to half.

In some embodiments, the collimators 110-I and 110-II are separated pieces. For example, the collimator 110-I is mounted to the detector tile 108-I such that both move (e.g., rotate or tilt) together, and similarly the collimator 110-II is mounted to the detector tile 108-II. Therefore, when the actuators 216 extend to tilt the detector tiles, each collimator is tilted accordingly together with the respective detector tile. In alternative embodiments, the collimators 110-I and 110-II are fabricated as one piece with a fixed angle β. The detector tiles 108-I and 108-II are tilted first without the collimators attached. After the detector tiles 108-I and 108-II have been tilted to the predetermined angle (β1+β2=β), the collimators 110-I and 110-II are then mounted above thereafter manually or automatically with robotic arms.

Figure 8:
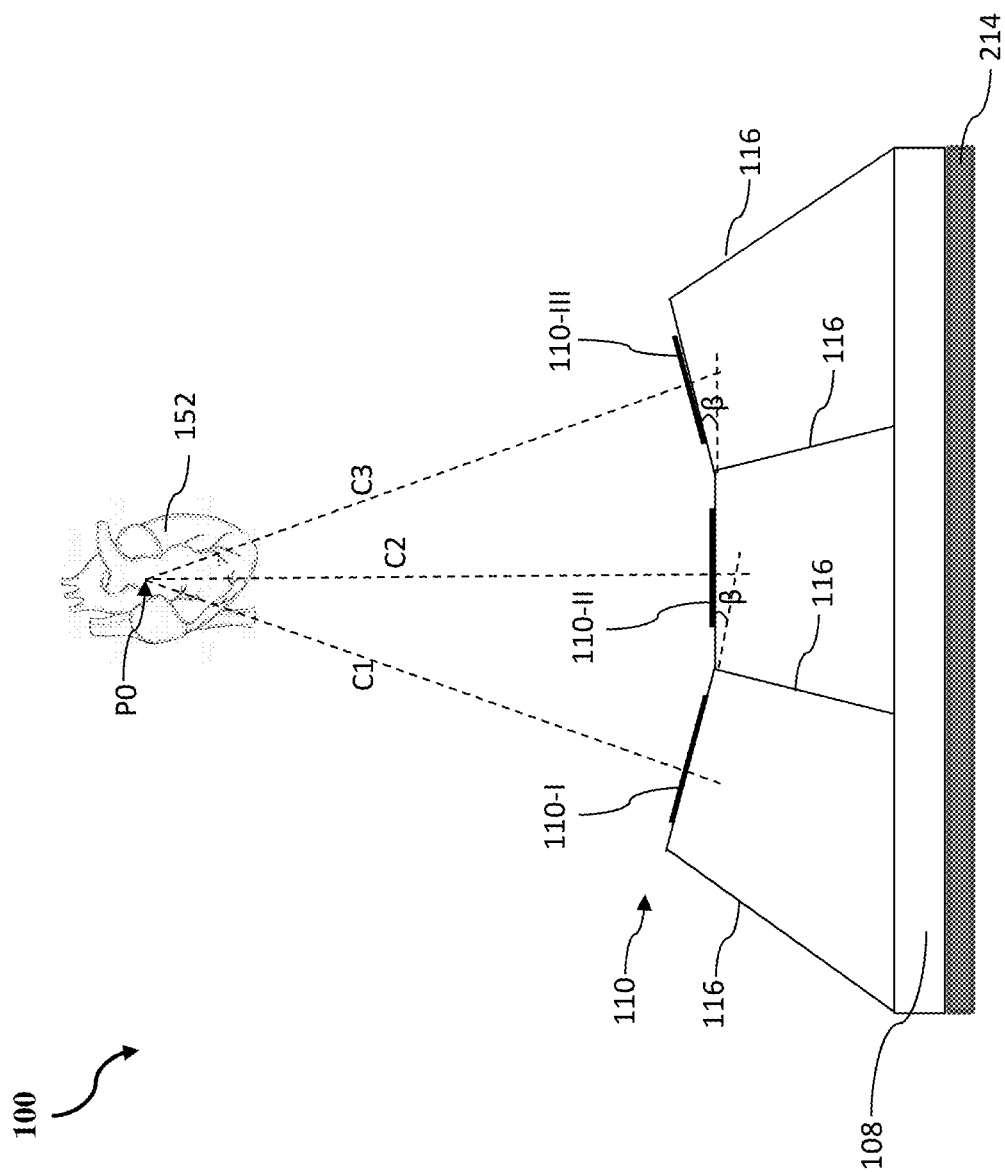
FIG. 8 is a cross-sectional view of an imaging system with a planar detector and tilted collimator parts according to various aspects of the present disclosure.

In some other embodiments, the detector 108 may stay planar without being bent or tilted, while the collimator 110 comprises multiple parts that are positioned at small angles and there are portions of the detector that are designated to receive radiations from each of these parts of collimator (these designated portions of detector may overlap slightly), such as shown in FIG. 8. Similar to what has been discussed above in association with FIG. 7, the FOV of such angularly placed collimators are overlapping. In some embodiments, the normal lines of these collimators (lines perpendicularly passing through the center of the collimators, denoted as dotted lines C1, C2, and C3 in FIG. 8) intersect at one common point (or a relatively small volume in space where the organ located), which defines the center of FOV of the system in such configuration. In the illustrated embodiment, imaging can be done in one third of the original detector rotations. Since the design works in the case of detector not bending, this design works with conventional systems employing detectors that are not bendable, making it applicable to current systems that employ unbendable detectors. Note that in this embodiment, the collimator parts 110-I/II/III may not be parallel to the detector surface. Here "not be parallel" is referred to as having an angle formed between the collimator and the detector surfaces that is larger than the tolerance of mechanical assembly inaccuracy, such as an angle larger than 1 degree, or an angle larger than 3 degrees. The collimator 110 (including collimator parts 110-I/II/III) is considered as piece-wise planar, such that each collimator part is planar, while some adjacent collimator parts (portions with holes) are not coplanar. The collimator 110 may be fabricated as one piece, or as two or three separate pieces and mounted separately. Since the detector 108 does not bend, it may be easier just making the collimator 110 as one piece, and there may be still shielding plates 116 in between to separate the collimator parts 110-I/II/III, preventing radiations passing though one collimator and hitting portions of detector designated to receive radiations passing through another collimator.

Figure 9:
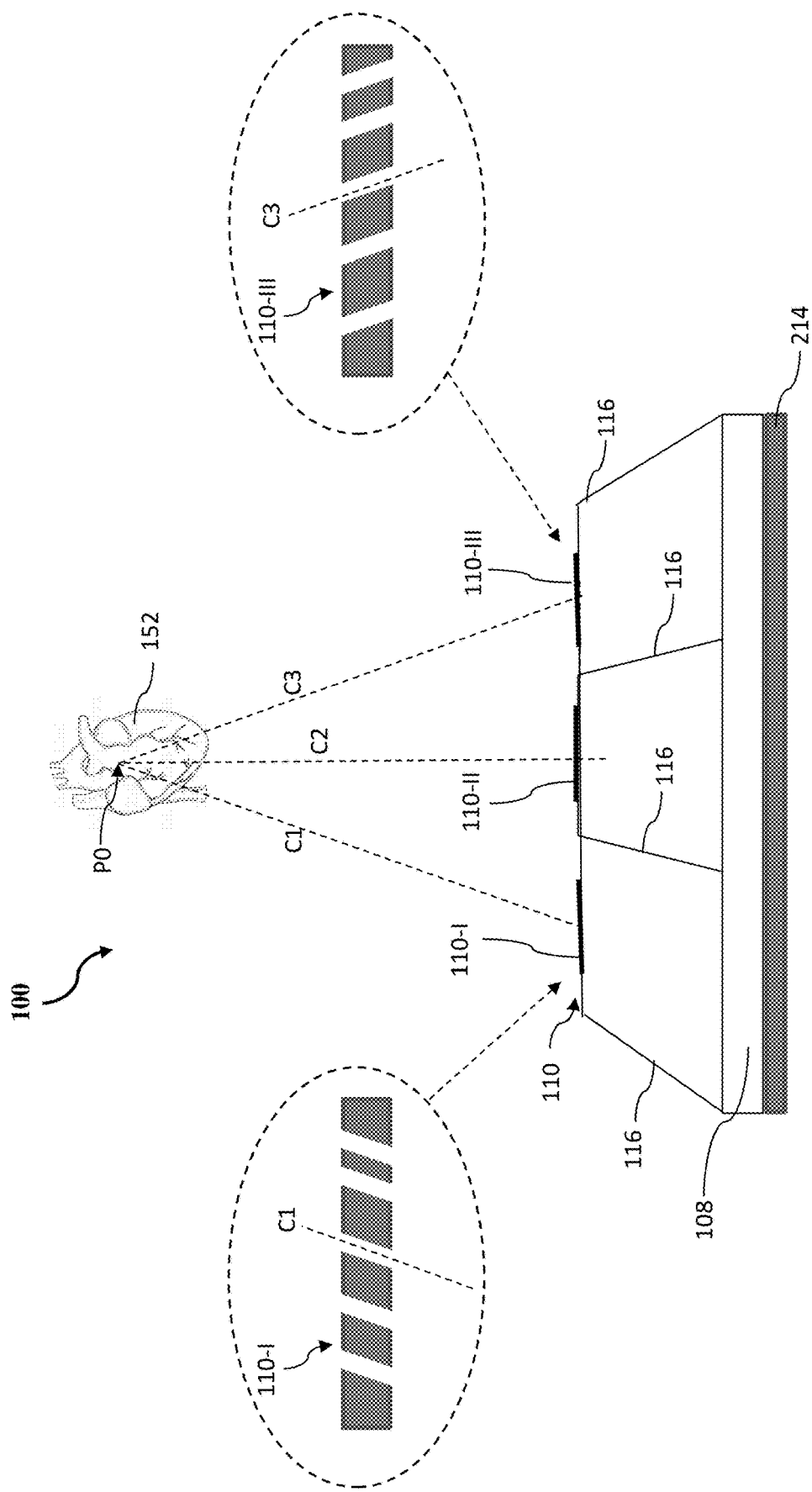
FIG. 9 is a cross-sectional view of an imaging system with a planar detector and a planar collimator with tilted holes according to various aspects of the present disclosure.

In yet another embodiment, similar to the previous embodiment, but the collimator may be in planar shape, and comprises multiple parts and each part with a group of holes that are tilted by a small angle, and pointing to the designed FOV, as shown in FIG. 9. In this case, the collimator surface may be parallel to the detector surface that may be in planar shape as well. And the holes in each collimator part (110-I, II, or III) may be parallel to each other. In the illustrated embodiment, holes in the collimator parts 110-I and 110-III are tilted, such that dotted lines C1 and C3 through centers of respective collimator parts and parallel to holes' elongated direction intersect at common point $P_O$. While holes in the middle collimator part 110-II extend along its normal direction, such as the holes shown in FIG. 2 and respective dotted line C2 through the center of the middle collimator part extends along the normal direction and goes through common point $P_O$ as well.

Figure 10:
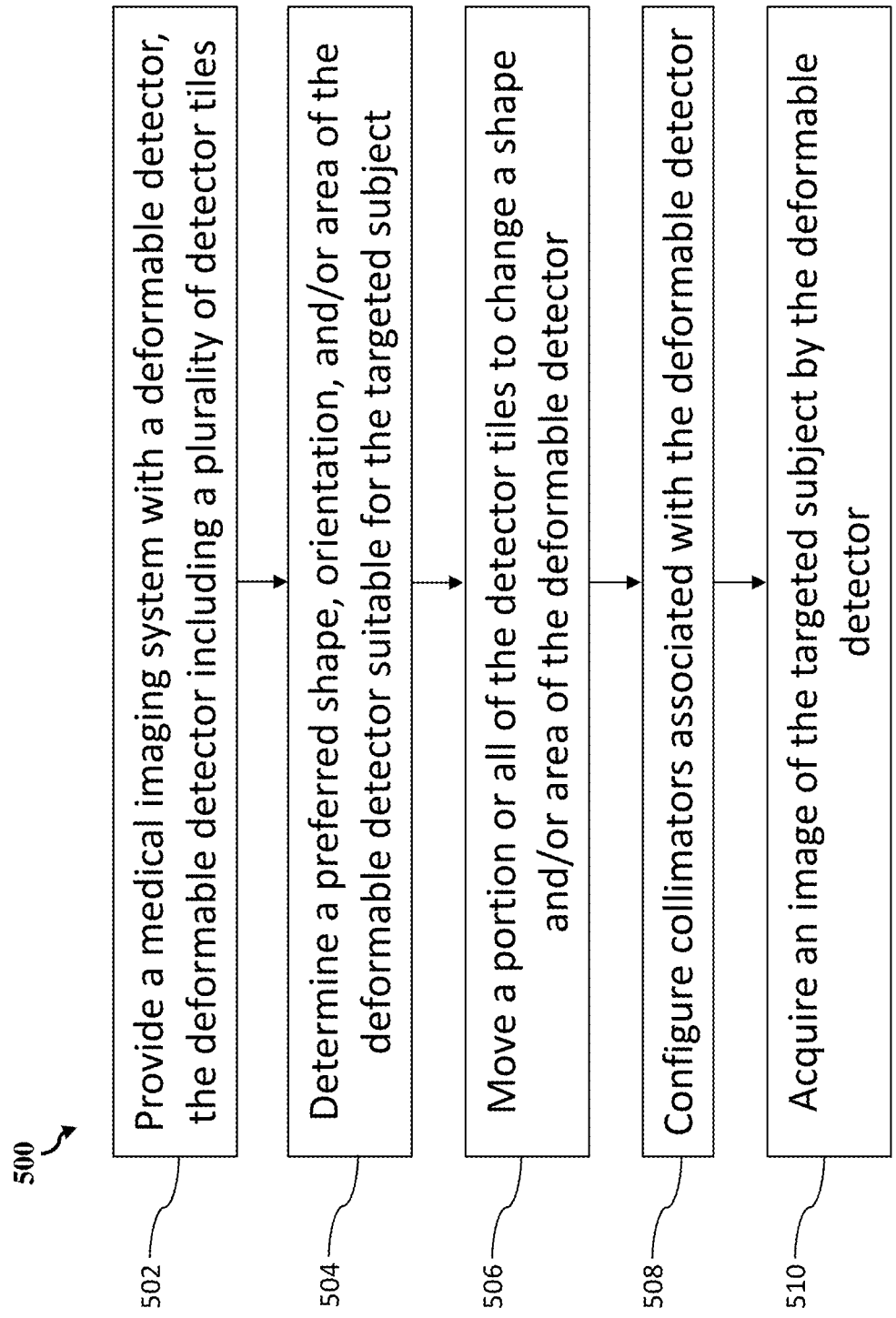
FIG. 10 is a flow chart of a method of examining a subject according to various aspects of the present disclosure.

Referring now to FIG. 10, a flow chart of a method 500 for acquiring a subject image with deformable detector is illustrated according to various aspects of the present disclosure. The method 500 is merely an example and is not intended to limit the present disclosure to what is explicitly illustrated in the method 500. Additional operations can be provided before, during, and after the method 500, and some operations described can be replaced, eliminated, or moved around for additional embodiments of the method. The method 500 is described below in conjunction with FIGS. 1-8.

At operation 502, a medical imaging system equipped with at least one deformable detector is provided. The deformable detector further includes multiple detector tiles. The medical imaging system, deformable detector, and detector tiles are similar to the imaging system 100 illustrated in FIG. 1, the deformable detector 108 illustrated in FIG. 4, and the detector tile illustrated in FIG. 3. Similar aspects are not repeated below in the interest of conciseness.

At operation 504, a preferred shape, orientation, and/or area of the deformable detector is determined. The consideration may include size and/or shape of the targeted subject, such as a patient, or a particular organ or body part of the patient. The other consideration may include distance from the targeted subject to the detector. In some embodiments, operation 504 picks from a group of predetermined detector configurations.

At operation 506, the detector rotates along its normal axis (perpendicular to the detector), or a portion of the detector tiles are moved, such as by moving the selected detector tiles along tracks. For example, operation 506 may only need to move one detector tile, while other detector tiles remain fixed. Or, two or more detector tiles would be moved. Or, all detector tiles will be moved. Operation 506 may also batch a few detector tiles in a group, such that detector tiles belonged to the same group are moved together while remain relatively fixed to each other within the group. In one embodiment, the top surfaces of the detector tiles are configured to be coplanar during deformation, in other words, the top surface of the deformable detector is kept flat (also termed as the deformable detector is planar), while the shape (e.g., geometry or aspect ratio is changed as in FIGS. 6A-6D) and/or orientation (e.g., same shape but rotated as in FIGS. 5C and 5D) is changed. In another embodiment, one or more detector tiles are moved to edges of the deformable detector, or moved away from the other part of the deformable detector at a certain distance, or moved to stack behind other detector tiles, and shut off, which equivalently reduces effective area of the deformable detector. In yet another embodiment, a portion of the detector tiles are tilted to form a non-flat detector, such as illustrated in FIG. 7.

At operation 508, collimators associated with the deformable detector are configured. In one embodiment, each collimator is fixed to the respective detector tile, such that the collimator is moved or tilted together with the detector tile mounted thereon. Alternatively, the collimators may be assembled or mounted above the detector tiles after the detector deformation is completed.

At operation 510, the medical imaging system acquires images of the targeted subject by detecting or monitoring amount of radiation collected by the deformable detector. An image processing unit in the medical imaging system may perform an image reconstruction based on the raw images acquired from the deformable detector.

Although not intended to be limiting, one or more embodiments of the present disclosure provide many benefits for molecular imaging of a subject such as a patient. For example, the deformable detectors allow an imaging system to gain flexibility in spatial resolution and increase step-and-scan efficiency when acquiring 3D images. Therefore, system performance is improved.

The foregoing outlines features of several embodiments so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure. Accordingly, it is appropriate that the appended claims be construed broadly and in a manner consistent with the present disclosure.

What is claimed is:

1. A medical imaging system, comprising:
a collimator having a plurality of collimator parts configured to filter radiation emitted from a target object;
a detector base; and
a detector having a plurality of detector tiles, configured to acquire an image of the target object by detecting radiation that has passed through the plurality of collimator parts, wherein at least one of the plurality of detector tiles is tilted with respect to the detector base.

2. The medical imaging system of claim 1, wherein each of the plurality of detector tiles has a field of view and the fields of view overlap.

3. The medical imaging system of claim 1, further comprising at least one shielding plate positioned between the plurality of detector tiles.

4. The medical imaging system of claim 1, wherein the at least one tilted detector tile is tilted by an actuator positioned between the detector base and the at least one tilted detector tile.

5. The medical imaging system of claim 1, wherein the plurality of collimator parts are hingedly linked.

6. The medical imaging system of claim 1, wherein at least one of the plurality of collimator parts includes through holes that form a coded aperture or an extended coded aperture.

7. The medical imaging system of claim 1, wherein each of the plurality of collimator parts is mounted to a respective one of the plurality of detector tiles such that each of the plurality of collimator parts moves with its respective detector tile.

8. The medical imaging system of claim 1, wherein each of the plurality of detector tiles corresponds to one of the plurality of collimator parts, and wherein at least one of the plurality of collimator parts is not parallel with respect to a top surface of its corresponding detector tile.

9. The medical imaging system of claim 1, wherein each of the plurality of detector tiles corresponds to one of the plurality of collimator parts, and wherein both of the plurality of collimator parts are parallel with respect to a top surface of its corresponding detector tile.

10. The medical imaging system of claim 1, wherein normal lines of the plurality of collimators parts intersect at a common point, the common point defining a center of a field of view of the medical imaging system.

11. The medical imaging system of claim 10, wherein the detector is rotatable, and wherein the center of the field of view remains at a same location when the detector is rotated.

12. The medical imaging system of claim 1, wherein a plurality of detector tiles are tiled with respect to the detector base.

13. The medical imaging system of claim 12, wherein the plurality of detector tiles are tilted with respect to the detector base at a same angle.

14. The medical imaging system of claim 12, wherein the plurality of detector tiles are tilted with respect to the detector base at different angles.

15. The medical imaging system of claim 1, wherein at least one of the plurality of detector tiles is not tilted with respect to the detector base.

16. The medical imaging system of claim 1, wherein the plurality of detector tiles are hingedly linked.

17. The medical imaging system of claim 1, wherein the plurality of detector tiles are spaced apart by a gap.

18. The medical imaging system of claim 17, wherein the gap is smaller than a width of at least one of the plurality of detector tiles.

19. The medical imaging system of claim 1, wherein the detector base is a common detector base shared by the plurality of detector tiles.

20. The medical imaging system of claim 1, further comprising at least one shielding plate positioned radially outward with respect to at least one of the plurality of collimator parts.

* * * * *